US006309418B1

(12) United States Patent
Jobe

(10) Patent No.: US 6,309,418 B1
(45) Date of Patent: Oct. 30, 2001

(54) REDUCED PROFILE EYELID WEIGHTING SYSTEM

(75) Inventor: Richard P. Jobe, Scotts Valley, CA (US)

(73) Assignee: MedDev Corporation, Sunnyvale, CA (US)

( * ) Notice: Subject to any disclaimer, the term of this patent is extended or adjusted under 35 U.S.C. 154(b) by 0 days.

(21) Appl. No.: 09/590,194

(22) Filed: Jun. 8, 2000

(51) Int. Cl.$^7$ ........................................................ A61F 2/14
(52) U.S. Cl. ................................................................. 623/4.1
(58) Field of Search ............................... 623/4.1; 128/898

(56) References Cited

U.S. PATENT DOCUMENTS 5,542,437 * 8/1996 Blackmore et al. .................. 128/899

OTHER PUBLICATIONS

MedDev Corporation, "Gold Eyelid Implants; Contour Design," MedDev Corporate brochure, 1998.*
Barclay et al., "Restoration of Movement to the Upper Eyelid in Facial Palsy," British Journal of Plastic Surgery 22, 1969, pp. 257–261.*
Jobe, "A Technique of Lid Loading in the Management of Lagophthalmos of Facial Palsy," Plastic and Reconstructive Surgery, vol. 53, No. 1, 1974, pp. 29–32.*
Seiff, et al., "Pretarsal Fixation of Gold Weights in Facial Nerve Palsy," Ophthalmic Plastic and Reconstructive Surgery, vol. 5, No. 2, 1989, pp. 104–109.*
Kartush et al., "Early Gold Weight Eyelid Implantation for Facial Paralysis," Otolaryngology—Head and Neck Surgery, vol. 103, No. 6, 12/90, pp. 1016–1023.*
Sobol et al., "Early Gold Weight Lid Implant for Rehabilitation of Faulty Eyelid Closure with Facial Paralysis; an Alternative to Tarsorrhaphy," Head and Neck Surgery, Mar./Apr. 1990, pp. 149–153.*
Petruzzelli et al., "Bell's Palsy, a Diagnosis of Exclusion," Postgraduate Medicine vol. 90, No. 2, 8/91, pp. 115–127.*
Seiff et al., "Management of Ophthalmic Complications of Facial Nerve Palsy," Otolaryngologic Clinics of North America, vol. 25, No. 3, 6/92, pp. 669–690.*
Townsend, "Eyelid Reanimation for the Treatment of Paralytic Lagophthalmos: Historical Perspectives and Current Applications of the Gold Weight Implant," Ophthalmic Plastic & Reconstructive Surgery, vol. 8, No. 3, 1992 pp. 196–201.*
Muller–Jensen et al., Zur Operativen und Konservatinen Behandlung des Lagophthalmus (Fazialisparese), Ophthamologe (1993) 90:27–30, English Summary, p. 30.*

* cited by examiner

Primary Examiner—Dinh X. Nguyen
(74) Attorney, Agent, or Firm—Flehr Hohbach Test Albritton & Herbert LLP

(57) ABSTRACT

A reduced profile eyelid weight longer and wider than traditional eyelid weights but thinner so as to provide a less protruding profile.

7 Claims, 1 Drawing Sheet

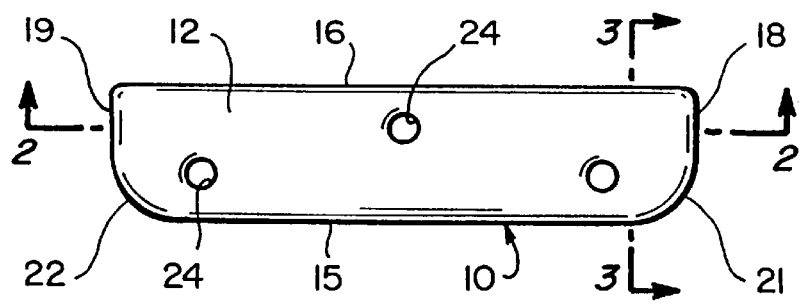
FIG_1
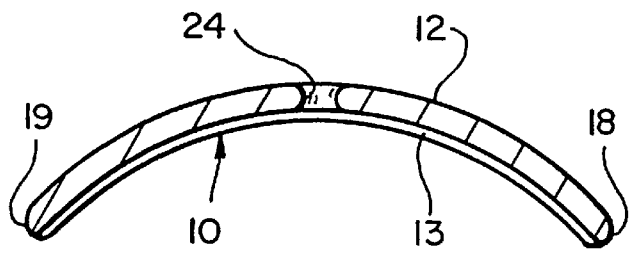
FIG_2
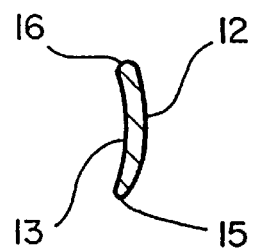
FIG_3
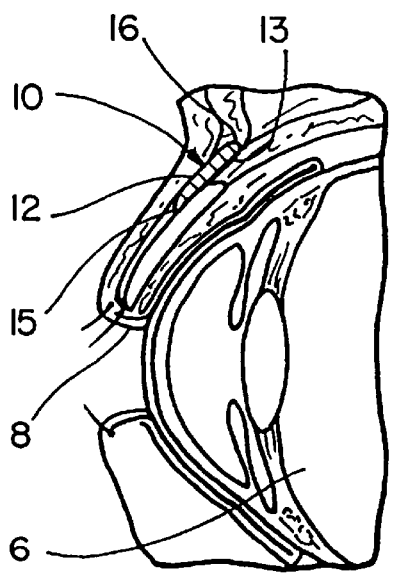
FIG_4A
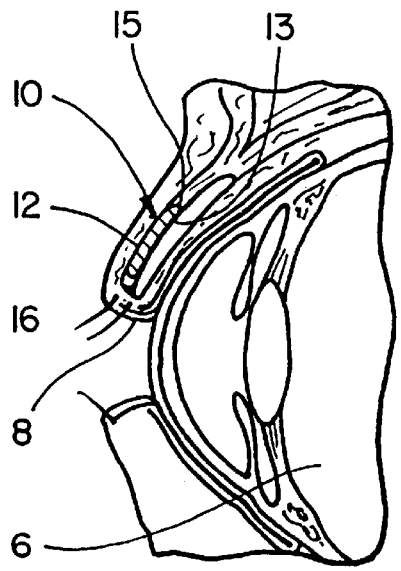
FIG_4B

REDUCED PROFILE EYELID WEIGHTING SYSTEM

FIELD

The present invention relates to a system for the treatment of lagophthalmos and, more particularly, to an eyelid weighting device for improving eyelid closure and reduced profile for a less conspicuous implant.

BACKGROUND

A number of different eyelid closure systems exist for facial paralysis. Surgical procedures, such as tarsorrhaphy (suturing the corners of the eyelids together) and implanting various prosthetic devices in the eyelids may be used to improve eyelid closure and reduce exposure of the eye. This provides some protection but generally prevents eyelid closure, reduces peripheral vision, and may be cosmetically unattractive. Prosthetic devices such as tantalum gauze mesh, silicon rubber elastic strips, stainless steel springs and magnets implanted in the upper and lower lids provide some amount of active eyelid closure.

Gold weight implants are also used in the surgical treatment of facial paralysis. The gold weights are implanted in the upper eyelid and secured to either the tarsal plate, orbital septum, or levator aponeurosis. When the levator muscle is relaxed, the upper eyelid is lowered by the force of gravity. One problem with the implants is the noticeable protrusion through the skin of the eyelid, an undesirable cosmetic effect. U.S. Pat. No. 5,543,437 discloses a standard profile weight. What is needed is an implant with a reduced profile. Although the profile is reduced the implant must maintain the same weight in order t o properly lower the eyelid.

SUMMARY

It is a general object of the invention to provide a reduced profile eyelid weight. It is a further object of the present invention to provide an eyelid weight with a reduced profile yet with a useable range of weight for eyelid closure.

BRIEF DESCRIPTION OF THE DRAWINGS

Additional advantages of the invention will become apparent upon reading the following detailed description and upon reference to the drawings, in which:

FIG. 1 is a top plan view of an eyelid weighting device in accordance with the present invention.

FIG. 2 is a cross-sectional view taken along line 2—2 in FIG. 1.

FIG. 3 is a cross-sectional view taken along line 3—3 in FIG. 1.

FIG. 4a and 4b are schematic views showing the placement of the weighting device when implanted in the eyelid.

DETAILED DESCRIPTION

The exemplary embodiments are described herein with reference to specific configurations and protocols. Those skilled in the art will appreciate that various changes and modifications can be made to the exemplary embodiments while remaining within the scope of the present invention. This invention incorporates by reference the teaching in U.S. Pat. No. 5,543,437.

A first embodiment is described with reference to FIGS. 1 to 4b. An eyelid weighting device or implant 10 incorporating the invention is shown in FIGS. 1–3. The implant 10 is a bar with an outer surface 12 and a concave inner surface 13. The concave surface 13 has a substantially spherical curvature which conforms to the curvature of the eyeball or globe 6. The outer surface 12 preferably follows the general shape of the inner surface 13 as shown to reduce the visibility of the implant 10 in the eyelid. In the preferred form the concave surface 13 has a radius of curvature of between approximately 11.5 to 13.5 mm, for example approximately 12.7 mm.

When the weighting device 10 is implanted in an eyelid 8, the spherical shape of inner surface 13 provides for substantially unrestrained movement of the implant 10 across the surface of the eye when the lid is opened and closed. With the concave surface 13 the inducement of astigmatism is minimized and the implant 10 is more comfortable for the patient as the weight of the implant 19 is not concentrated at the edges of the implant 10, but is instead evenly distributed across the area of the eye beneath the surface 13. Eyelid closure without induced astigmatism is made more effective by the spherical shape of surface 13, protecting the eye from dryness, irritation and other potentially damaging conditions.

Implant 10 has a pair of spaced, first and second major edges 15 and 16 and a pair of side edges 18 and 19. The first major edge 15 has contoured ends 21 and 22 which are curved upward and outward toward the side edges 18 and 19. The radius of curvature of the contoured ends is preferably in the range of approximately 2 to 3.5 mm. Providing the first major edge 15 with contoured ends reduces the surface area of the inner and outer surfaces 12 and 13 so that the implant is less visible in the eyelid. The first major edge 15 is also tapered as shown in FIG. 3. Reducing the thickness of the implant along the first major edge further lowers the profile of the implant within the lid where the eyelid skin is thinnest. The spherical-shaped implant 10 is less noticeable, a feature that is particularly desirable for the more self-conscious patient.

The edges 15, 16, 18 and 19 are preferably rounded or smoothed to remove any sharpness and minimize the risk that the implant will extrude through the surface of the lid. Providing the edges of the weighting device 10 with a smooth finish also enhances the comfort of the implant.

One or more apertures 24 are formed in the weighting device 10 as shown in FIG. 1. The apertures may be used to anchor the implant 10 to the orbital septum or tarsus, placing it securely parallel to the eyelid margin, depending upon the final placement of the implant in the lid. Sutures may be inserted through one or more of the apertures 24 and fixed to the appropriate tissues. A suture through a second or third aperture may be required to ensure secure placement parallel to the eyelid margin. After time, the placement of the implant 10 is further stabilized by tissue growth through the apertures 24. The number of apertures formed in implant 10 may vary, although three apertures are generally suitable for implants with dimensions of 11.3 mm to 18.2 mm in length and 5.5 to 6.5 mm in height.

The implant 10 has a thickness of approximately 0.5 to 0.7 mm, and a width of approximately 5 to 7 mm. The nominal length of the implant varies depending upon the weight of the implant and the material from which the implant is fabricated. Suitable materials include gold or platinum. Gold is preferred due to its high specific gravity and color. Platinum is preferred if there is an allergic reaction to gold. The most useful weights vary from 0.6 to 1.6 grams.

The weighting device 10 is implanted using the appropriate surgical techniques. The placement of the implant 10 may be septal (FIG. 4a) or pretarsal (FIG. 4b) depending on the preference of the surgeon and the needs of the patient. Septal placement is often preferred as the implant is less conspicuous, although some prefer lower pretarsal placement. When fixed to the orbital septum the implant is oriented with the first major edge 15 facing downward as shown particularly in FIG. 4a. The first major edge 15 may face upward, as shown in FIG. 4b, or downward when the implant 10 is secured to the tarsus. Orienting the implant 10 as described ensures that the contoured ends 21 and 22 and the tapered portion of the implant are situated in the thinnest portion of the eyelid.

Having disclosed exemplary embodiments and the best mode, modifications and variations may be made to the disclosed embodiments while remaining within the scope of the present invention as defined by the following claims.

What is claimed is:

1. An eyelid weight comprising an elongated bar with a concave inner surface, first and second major edges, one of said major edges being tapered so that the bar is thinner at the said major edge, said bar having tapered ends, said major edge being contoured at its ends so that it merges with the ends of the bar, said bar having a length from 11 to 19 millimeters, a width from 5 to 7 millimeters, and a maximum thickness of less than 0.7 millimeters.

2. The eyelid weight of claim 1 wherein the maximum thickness is from 0.5 to less than 0.7 millimeters.

3. The eyelid weight of claim 1 wherein the thickness is 0.6 millimeters.

4. The eyelid weight of claim 1 wherein the concave inner surface has a radius of curvature of approximately 12.7 millimeters.

5. The eyelid weight of claim 4 wherein the weight varies between 0.6 grams and 1.6 grams.

6. The eyelid weight of claim 5 wherein the concave bar is shaped in three dimensions in order to simulate the shape of the eyeball.

7. The eyelid weight of claim 6 wherein the concave bar has rounded edges.

* * * * *